(12) United States Patent
Scheuerman et al.

(10) Patent No.: US 6,323,377 B1
(45) Date of Patent: Nov. 27, 2001

(54) OXIDATION PROCESS

(75) Inventors: Randall A. Scheuerman, Santa Clara; Clive A. Henrick, Palo Alto, both of CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/149,703

(22) Filed: Sep. 8, 1998

Related U.S. Application Data

(63) Continuation of application No. 08/473,883, filed on Jun. 7, 1995, now abandoned.

(51) Int. Cl.⁷ .............................. C07C 39/24; C07C 37/00
(52) U.S. Cl. ......................... 568/774; 568/716; 568/797; 568/803
(58) Field of Search .................................. 568/774, 716, 568/797, 803

(56) References Cited

U.S. PATENT DOCUMENTS

| | | |
|---|---|---|
| 3,013,054 | 12/1961 | Richter . |
| 4,529,824 | 7/1985 | Mimoun et al. . |
| 4,798,837 | 1/1989 | Drabek et al. . |
| 5,648,562 * | 7/1997 | Henrick . |

FOREIGN PATENT DOCUMENTS

| | | |
|---|---|---|
| 21 01 992 | 8/1972 | (DE) . |
| 0 179 022 | 4/1986 | (EP) . |
| 1 428 271 | 3/1976 | (GB) . |
| 92/18449 | 10/1992 | (WO) . |

OTHER PUBLICATIONS

Tetrahedron, vol. 52, No. 11, 1996, pp. 3889–3896, Fujimoto et al.

Journal of Molecular Catalysis, vol. 83, No. 1–2, 1993, pp.107–116, Bianchi et al.

Derwent Abstract No. 52216T–E (of DE 21 01 992) Mar. 8, 1972.

* cited by examiner

Primary Examiner—Paul J. Killos
(74) Attorney, Agent, or Firm—William A. Teoli, Jr.

(57) ABSTRACT

Preparation of 2,5-dichlorophenol by selectively oxidizing 1,4-dichlorobenzene using a peroxo-, hydroperoxo-, superoxo- or alkylperoxo-metal species in the presence of form or an alkanoic acid.

31 Claims, No Drawings

OXIDATION PROCESS

The instant application is a continuation of application Ser. No. 08/473,883 filed Jun. 7, 1995, now abandoned.

The present invention concerns the selective oxidation of 1,4-dichlorobenzene to 2,5-dichlorophenol.

U.S. Pat. No. 4,529,824 describes in general certain complexes of vanadium, niobium and tantalum and their use in hydroxylating aromatic hydrocarbons either as reactant or catalyst. Additionally, Moiseeva et al. Kinet. Katal 29(4), 970–4 (1988) describe oxidation of benzene with vanadium compounds albeit not selectively for phenol (oxidation proceeds at least in part to quinone).

It has now surprisingly been found that oxidation of 1,4-dichlorobenzene to 2,5-dichlorophenol can be effected with high yield and selectivity when carried out in the presence of certain metal derivatives and in the presence of formic or an alkanoic acid.

The present invention therefore provides a process for the preparation of 2,5-dichlorophenol which comprises selectively oxidizing 1,4-dichlorobenzene using an oxidizing agent and a peroxo-, hydroperoxo-, superoxo- or alkylperoxo-metal species wherein said metal is selected from scandium, yttrium, lanthanum, titanium, zirconium, hafnium, vanadium, niobium, tantalum, chromium, molybdenum, tungsten, manganese, rhenium, iron, ruthenium, selenium, tellurium, osmium, cobalt, rhodium, iridium, nickel, palladium, platinum, copper, silver, zinc, aluminum, gallium, indium, tin, cerium, praseodymium, neodymium, samarium, europium, gadolinium, terbium, dysprosium, holmium, erbium, thulium, ytterbium, lutetium, and uranium or mixtures thereof in the presence of an acid selected from formic or an alkanoic acid.

The oxidation may be effected using an oxidation agent. Suitable oxidation agents included organic peroxides such as peroxycarboxylic acids, $RCO_3H$, alkyl hydroperoxides, ROOH, and dialkylperoxides, ROOR, for example peroxyacetic acid, peroxybenzoic acid, peroxyformic acid, t-butyl hydroperoxide, and di-t-butylperoxide and inorganic peroxides such as peroxydisulfuric acid. The preferred peroxide for use in the invention however, is hydrogen peroxide, especially in aqueous solution. The present process can be carried out at dilutions of 3% to 90% with almost complete utilization of $H_2O_2$ and quantitive yields. However, ca 50% aqueous $H_2O_2$ is preferred. The proportions of $H_2O_2$ to 1,4-dichlorobenzene may vary between 0.2 and 5, e.g. between 0.5 and 2. It has been determined that particularly high efficiency may be achieved using approximately equimolar amounts of $H_2O_2$ and 1,4-dichlorobenzene, e.g. ca 0.9 to ca 1.1 molar proportion of $H_2O_2$ per mole of 1,4-dichlorobenzene.

The peroxo-, hydroperoxo-, superoxo- or alkylperoxo-metal species may be and preferably is generated in situ by adding the desired metal either as pure metal or in the form of a suitable oxide, salt or other derivative. Alternatively, the desired derivative e.g. an acetoacetonate may be formed prior to reaction and added to the reaction mixture.

Suitable metal forms include oxides, anhydrides, acetylacetonates, alkoxymetal derivatives, sulfates, nitrates, halides, oxyhalides, alkylthiocarbamates or metalates with other cations, (e.g. ammonium metavanadate $NH_4VO_3$)

Preferred metals include molybdenum, titanium, vanadium, tungsten, rhenium, selenium, niobium, tantalum and tellurium with vanadium being particularly preferred.

Preferred metal forms include oxides, acetylacetonates, alkoxymetal oxides and oxychlorides.

A discussion of peroxo-, hydroperoxo-, superoxo- and alkylperoxo-metal species can be found in Conte et al. in Organic Peroxides Ed. W. Ando, John Wiley & Sons (1992) (pp 559–598).

Discussion of hydroperoxide oxidising agents and metal derivatives may also be found in U.S. Pat. Nos. 3,350,422; 3,351,635; 3,360,584; 3,360,585; and 3,662,006.

A particular advantage of the present process is that the peroxo-, hydroperoxo-, superoxo- or alkylperoxo-metal species can be and preferably are free of complex ligands.

The metal derivatives can be present in amount equivalent to between 0.001 and 100 mol % of metal. Preferably catalytic amounts of 0.1 to 15 mol % are employed.

When employed as a catalyst the metal derivative may be recycled and regenerated. For example when an oxide such as vanadium pentoxide is used the spent catalyst can be heated in air (cf Polish Patent PL 73-165695; C.A. 87.91418) or treated with hydrogen peroxide.

The acid component of the process according to the invention is selected from formic or an alkanoic acid. Preferred alkanoic acids are lower alkanoic acids containing e.g. 2 to 6 carbon atoms such as acetic, propionic or butyric acid. The preferred acid according to the invention is acetic acid.

The use of solvents may also have a beneficial effect on the process according to the invention. Examples of such solvents include aprotic solvents such as chlorinated solvents e.g. 1,2-dichloromethane, dichloromethane, chloroform, nitrated solvents, e.g. nitromethane; nitrites e.g. acetonitrile, propionitrile, benzonitfile; ketones, e.g. acetone, methylethylketone; alkanes, e.g. hexane; esters e.g. ethylacetate; alcohols e.g. methanol, ethanol, isopropanol; or mixtures thereof.

Reaction temperatures lie between 0 and 150° C. and are preferably in the range of room to elevated (ca 90°) temperature e.g. when employing acetic acid and a vanadium derivative. The reaction is preferably carried out in the substantial absence of water. In certain cases removal of water further increases yield. This is the case for example where the oxidising agent is used in aqueous solution or where the water is generated during the reaction. Removal of water can be achieved for example by carrying out the reaction in the presence of a drying agent such as activated molecular sieves (3 Å or 4 Å), calcium sulphate, magnesium sulphate or acetic anhydride, etc.

In certain cases pH will affect the course of the reaction and therefore the addition of a Lewis acid or a Bronsted acid (cf Kirk Othmer Encyclopedia of Chemical Technology; 4th Edition; Wiley lnterscience) such as p-toluenesulfonic or methanesulfonic acid can increase the yield.

Addition of a salt of the chosen formic or alkanoic acid e.g. dry sodium acetate with acetic acid can increase the yield in certain cases.

The reaction mixture may be mono- or multi- e.g. bi-phasic. Examples of such systems can be found in Bianchi et al. J. Mol. Catal. 83 (1993) 107–116; Bonchio et al. J. Org. Chem. 54 (1989) 4368–4371.

Typically the substrate to be oxidised (1,4-dichlorobenzene) is dissolved in the chosen acid (e.g. acetic acid) and the metal derivative (e.g. a high valency oxide) added followed by the slow addition of the oxidising agent (e.g. aqueous $H_2O_2$). The metal derivative may be deposited on a carrier such as silica, alumina, aluminosilicates, zeolites, coals, titanium oxide, quartz, etc.

The starting material 1,4-dichlorobenzene has the formula

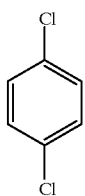

and is a known, commercially available substance.

The desired end product 2,5-dichlorophenol has the formula

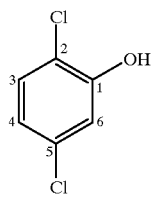

and is useful as an intermediate in the preparation of the commercial herbicide dicamba in high isomeric purity (e.g. in substantial absence of 3,5-dichloro-o-anisic acid).

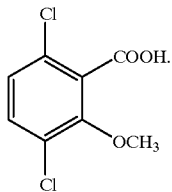

This process involves carboxylation of the 2,5-dichlorophenol to give 2-hydroxy-3,6-dichlorobenzoic acid (a.k.a. 3,6-dichlorosalicylic acid) and methylation of this substrate with subsequent saponification to give high purity dicamba which may be isolated in free acid, salt or ester form (cf e.g. U.S. Pat. No. 3,013,054 for reaction from 2,5-dichlorophenol to dicamba).

The relevant portions of publications and other patent documents cited herein are hereby also incorporated by reference.

The following examples illustrate the invention. Temperatures are in degrees centigrade.

EXAMPLE 1

To a solution of 1.47 g (10 mmol) of 1,4-dichlorobenzene dissolved in 20 mL of acetic acid is added with stirring 0.182 g (1 mmol) vanadium(V) oxide followed by the gradual infusion of 2mL of 50% aqueous hydrogen peroxide (30 mmol) over 8 hours. After 24 hours at 20° C. the solid is removed by filtration, and washed with methanol. The combined filtrates are treated dropwise with concentrated aqueous sodium bisulfite to destroy any residual hydrogen peroxide and the solvents are removed in vacuo to give the desired product. This may be purified e.g. by vacuum distillation (b.p. 70° C. at 2 mm pressure) to give 2,5-dichlorophenol, m.p. 57–59° C.

EXAMPLE 2

To a solution of 1.47 g (10 mmol) of 1,4-dichlorobenzene dissolved in 20 mL of acetic acid is added with stirring 1.0 g of ~3.5 weight percent vanadium(V) oxide deposited on silica (0.2 mmol vanadium catalyst) the reaction is heated to 45° C. followed by the gradual infusion of 0.67 mL of 50% aqueous hydrogen peroxide (10 mmol) over 8 hours. After 16 hours at 45° C. the solid is removed by filtration, and washed with methanol. The combined filtrates are treated dropwise with concentrated aqueous sodium bisulfite to destroy any residual hydrogen peroxide and the solvents are removed in vacuo to give the desired product. This may be purified e.g. by vacuum distillation (b.p. 70° C. at 2 mm pressure) to give 2,5-dichlorophenol, m.p. 57–59° C.

EXAMPLE 3

To a solution of 1.47 g (10 mmol) of 1,4-dichlorobenzene dissolved in 20 mL of acetic acid is added with stirring 265 mg (1 mmol) vanadyl acetylacetonate followed by the gradual infusion of 2.0 mL of 50% aqueous hydrogen peroxide (30 mmol) over 8 hours. After 16 hours at 20° C. the solid is removed by filtration, and washed with methanol. The combined filtrates are treated dropwise with concentrated aqueous sodium bisulfite to destroy any residual hydrogen peroxide and the solvents are removed in vacuo to give the desired product. This may be purified e.g. by vacuum distillation (b.p. 70° C. at 2 mm pressure) to give 2,5-dichlorophenol, m.p. 57–59° C.

We claim:

1. A process for the preparation of 2,5-dichlorophenol which comprises selectively oxidizing 1,4-dichlorobenzene using an oxidizing agent and a peroxo-, hydroperoxo-, superoxo- or alkylperoxo-metal species (oxo-metal species), which oxo-metal species is substantially free of complex ligands, wherein said metal of said oxo-metal species is selected from the group consisting of scandium, yttrium, lanthanum, titanium, zirconium, hafnium, vanadium, selenium, tellurium, niobium, tantalum, chromium, molybdenum, tungsten, manganese, rhenium, iron, ruthenium, osmium, cobalt, rhodium, iridium, nickel, palladium, platinum, copper, silver, zinc, aluminum, gallium, indium, tin, cerium, praseodymium, neodymium, samarium, europium, gadolinium, terbium, dysprosium, holmium, erbium, thulium, ytterbium, lutetium, and uranium or mixtures thereof in the presence of an acid selected from formic or alkanoic acids.

2. The process according to claim 1 wherein the metal is selected from the group consisting of molybdenum, titanium, vanadium, tungsten, rhenium, selenium, niobium, tantalum, and tellurium.

3. The process according to claim 1 wherein the metal is vanadium.

4. The process according to claim 1 wherein the oxidizing agent is a peroxide.

5. The process according to claim 1 wherein the oxidizing agent is selected from the group consisting of a peroxycarboxylic acid, an alkylhydroperoxide, and a dialkylperoxide.

6. The process according to claim 1 wherein the oxidizing agent is hydrogen peroxide.

7. The process according to claim 1 wherein the acid is formic or a $C_2$–$C_6$ alkanoic acid.

8. The process according to claim 1 wherein the acid is acetic acid.

9. The process according to claim 1 wherein the peroxo-, hydroperoxo-, superoxo- or alkylperoxo-metal species is generated in-situ by adding pure metal or metal-oxide, salt, or other suitable form.

10. The process according to claim 9 wherein the metal is added in the form of an oxide, anhydride, acetylacetonate, alkoxymetal derivative, sulfate, nitrate, halide, oxyhalide, alkylthiocarbamate or metalate with other cations.

11. The process according to claim 10 wherein the metal form is an oxide, acetylacetonate, alkoxymetal oxide or oxychloride.

12. The process according to claim 1 wherein a Lewis acid or a Bronsted acid is additionally present.

13. The process according to claim 1 wherein a salt of the chosen formic or alkanoic acid is additionally present.

14. The process according to claim 1 wherein aqueous hydrogen peroxide at a dilution of 50% is used as the oxidizing agent.

15. A process for the preparation of 2,5-dichlorophenol which comprises selectively oxidizing 1,4-dichlorobenzene using an oxidizing agent and a peroxo-, hydroperoxo-, superoxo- or alkylperoxo-metal species (oxo-metal species) on a carrier, which oxo-metal species is generated by (a) depositing the oxo-metal species metal on a carrier and adding a peroxo- hydroperoxo-, superoxo-, or alkylperoxo containing component thereto, or (b) forming said oxo-metal species and depositing said oxo-metal species on said carrier, wherein said metal of said oxo-metal species is selected from the group consisting of scandium, yttrium, lanthanum, titanium, zirconium, hafnium, vanadium, selenium, tellurium, niobium, tantalum, chromium, molybdenum, tungsten, manganese, rhenium, iron, ruthenium, osmium, cobalt, rhodium, iridium, nickel, palladium, platinum, copper, silver, zinc, aluminum, gallium, indium, tin, cerium, praseodymium, neodymium, samarium, europium, gadolinium, terbium, dysprosium, holmium, erbium, thulium, ytterbium, lutetium, and uranium or mixtures thereof in the presence of an acid selected from formic or alkanoic acids.

16. The process according to claim 15 wherein the metal is selected from the group consisting of molybdenum, titanium, vanadium, tungsten, rhenium, selenium, niobium, tantalum, and tellurium.

17. The process according to claim 15 wherein the metal is vanadium.

18. The process according to claim 15 wherein the oxidizing agent is a peroxide.

19. The process according to claim 15 wherein the oxidizing agent is selected from the group consisting of a peroxycarboxylic acid, an alkylhydroperoxide, and a dialkylperoxide.

20. The process according to claim 15 wherein the oxidizing agent is hydrogen peroxide.

21. The process according to claim 15 wherein the acid is formic or a $C_2$–$C_6$ alkanoic acid.

22. The process according to claim 15 wherein the acid is acetic acid.

23. The process according to claim 15 wherein the peroxo-, hydroperoxo-, superoxo- or alkylperoxo-metal species is generated in-situ by adding pure metal or metal-oxide, salt, or other suitable form.

24. The process according to claim 23 wherein the metal is added in the form of an oxide, anhydride, acetylacetonate, alkoxymetal derivative, sulfate, nitrate, halide, oxyhalide, alkylthiocarbamate or metalate with other cations.

25. The process according to claim 24 wherein the metal form is an oxide, acetylacetonate, alkoxymetal oxide or oxychloride.

26. The process according to claim 15 wherein a Lewis acid or a Bronsted acid is additionally present.

27. The process according to claim 15 wherein a salt of the chosen formic or alkanoic acid is additionally present.

28. The process according to claim 15 wherein aqueous hydrogen peroxide at a dilution of 50% is used as the oxidizing agent.

29. A process for the preparation of 2,5-dichlorophenol which comprises selectively oxidizing 1,4-dichlorobenzene using an oxidizing agent and a peroxo-, hydroperoxo-, superoxo- or alkylperoxo-metal species (oxo-metal species), wherein said metal of said oxo-metal species is selected from the group consisting of scandium, yttrium, lanthanum, titanium, zirconium, hafnium, vanadium, selenium, tellurium, niobium, tantalum, chromium, molybdenum, tungsten, manganese, rhenium, iron, ruthenium, osmium, cobalt, rhodium, iridium, nickel, palladium, platinum, copper, silver, zinc, aluminum, gallium, indium, tin, cerium, praseodymium, neodymium, samarium, europium, gadolinium, terbium, dysprosium, holmium, erbium, thulium, ytterbium, lutetium, and uranium or mixtures thereof in the presence of an acid selected from formic or alkanoic acids, and wherein said metal of said oxo-metal species or a derivative of said metal is readily recyclable for regenerating said oxo-metal species.

30. A process for the preparation of 2,5-dichlorophenol which comprises selectively oxidizing 1,4-dichlorobenzene using an oxidizing agent and a peroxo-, hydroperoxo-, superoxo- or alkylperoxo-metal species (oxo-metal species) on a carrier, which oxo-metal species is generated by (a) depositing oxo-metal species metal on a carrier and adding a peroxo- hydroperoxo-, superoxo-, or alkylperoxo containing component thereto, or (b) forming said oxo-metal species and depositing said oxo-metal species on said carrier, wherein said metal of said oxo-metal species is selected from the group consisting of scandium, yttrium, lanthanum, titanium, zirconium, hafnium, vanadium, selenium, tellurium, niobium, tantalum, chromium, molybdenum, tungsten, manganese, rhenium, iron, ruthenium, osmium, cobalt, rhodium, iridium, nickel, palladium, platinum, copper, silver, zinc, aluminum, gallium, indium, tin, cerium, praseodymium, neodymium, samarium, europium, gadolinium, terbium, dysprosium, holmium, erbium, thulium, ytterbium, lutetium, and uranium or mixtures thereof in the presence of an acid selected from formic or alkanoic acids, and wherein said metal of said oxo-metal species or a derivative of said metal is readily recyclable for regenerating said oxo-metal species.

31. A process for the preparation of 2,5-dichlorophenol which comprises selectively oxidizing 1,4-dichlorobenzene using an oxidizing agent and a peroxo-, hydroperoxo-, superoxo- or alkylperoxo-metal species (oxo-metal species), wherein said metal of said oxo-metal species is selected from the group consisting of scandium, yttrium, lanthanum, zirconium, hafnium, selenium, tellurium, niobium, tantalum, chromium, molybdenum, tungsten, rhenium, ruthenium, osmium, rhodium, iridium, nickel, palladium, platinum, copper, silver, indium, tin, cerium, praseodymium, neodymium, samarium, europium, gadolinium, terbium, dysprosium, holmium, erbium, thulium, ytterbium, lutetium, and uranium or mixtures thereof in the presence of an acid selected from formic or alkanoic acids.

* * * * *